(12) United States Patent
Trippe et al.

(10) Patent No.: US 12,571,733 B2
(45) Date of Patent: Mar. 10, 2026

(54) UNBIASED SORTING AND SEQUENCING OF OBJECTS VIA RANDOMIZED GATING SCHEMES

(71) Applicant: Microsoft Technology Licensing, LLC, Redmond, WA (US)

(72) Inventors: Brian Loeber Trippe, Cambridge, MA (US); Lorin Anthony Crawford, Boston, MA (US); Kevin Kaichuang Yang, Cambridge, MA (US); Nicholas Bhattacharya, Berkeley, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1144 days.

(21) Appl. No.: 17/532,583

(22) Filed: Nov. 22, 2021

(65) Prior Publication Data

US 2023/0160824 A1 May 25, 2023

(51) Int. Cl.
*G01N 21/64* (2006.01)
*G16B 30/00* (2019.01)

(52) U.S. Cl.
CPC ..... *G01N 21/6428* (2013.01); *G01N 21/6458* (2013.01); *G16B 30/00* (2019.02); *G01N 2021/6439* (2013.01)

(58) Field of Classification Search
CPC ................ C12Q 2565/626; C12N 5/06; G01N 33/5005; G01N 33/48792; G01N 33/487;

(Continued)

(56) References Cited

U.S. PATENT DOCUMENTS

| | | | |
|---|---|---|---|
| 11,227,672 B2 * | 1/2022 | Lin | G01N 15/1459 |
| 2018/0136107 A1 * | 5/2018 | Li | G01N 15/1404 |

(Continued)

FOREIGN PATENT DOCUMENTS

| | | | |
|---|---|---|---|
| CN | 103454204 | * | 12/2013 |
| CN | 110444249 | * | 11/2019 |

(Continued)

OTHER PUBLICATIONS

Staats (Staats et al. (2019) Chapter 5: Guidelines for gating flow cytometry data for immunological assays. J Phillip McCoy Jr (ed.) Immunophenotyping: Methods and protocols; Methods in Molecular Biology, vol. 2032 (2019) Springer Science+Business Media, LLC. pp. 81-104.) (Year: 2019).*

(Continued)

*Primary Examiner* — Mary K Zeman
(74) *Attorney, Agent, or Firm* — Rainier Patent, P.S.

(57) ABSTRACT

Systems and methods are provided for sorting cells with distinct cell designs for characterizing a library of the cell designs. The present disclosure uses randomized sorting rules associated with bins and pseudo-random numbers to counts the cells with measured fluorescence values in one of the bins. A mean fluorescence value for a cell design group may be determined based on a ratio of cell counts of the cells associated with the cell design group across the bins. Unlike the traditional histogram-based sorting that use a mean fluorescence value of a bin, the disclosed technology determines mean fluorescence values of cell design groups for characterizing libraries of the cell design group. Use of the mean fluorescence values with unbiased "sort-seq" and a de-multiplexed sequencing using the mean fluorescence values enables characterizing libraries of cell designs with improved accuracy over traditional use of discrete histograms.

20 Claims, 7 Drawing Sheets

(58) Field of Classification Search

CPC .......... G01N 21/64; G01N 2021/6439; G01N 2021/6491; G01N 21/6428; G01N 2015/1006; G01N 21/6486; G01N 15/1429; G01N 15/0272; G01N 15/0266; G01N 2015/0288; G01N 2015/1024; G01N 2015/1028; G01N 15/14; G01N 2015/1402; G01N 15/1431; G16B 40/20; G16B 30/00; G16B 40/00; G16B 35/10; G16B 30/10; G16B 50/30; G16B 45/00; G16B 40/10; G16B 25/00; G16B 5/00; G16B 25/20; G16B 25/10

See application file for complete search history.

(56) References Cited

U.S. PATENT DOCUMENTS

| | | | |
|---|---|---|---|
| 2020/0126639 A1 | 4/2020 | Lin et al. | |
| 2023/0160824 A1* | 5/2023 | Trippe | ............... G01N 21/6428 |
| | | | 702/19 |

FOREIGN PATENT DOCUMENTS

| | | | | |
|---|---|---|---|---|
| CN | 110444249 A | 11/2019 | | |
| WO | WO-2022132985 A1 * | 6/2022 | ........... | G01N 5/1012 |
| WO | WO2023091293 | * | 5/2023 | |

OTHER PUBLICATIONS

Smith (Smith et al. (Sep. 2021) SorTn-seq: a high throughput functional genomics approach to discovering regulators of bacterial gene expression. Nature Protocols vol. 16, p. 4382-4418). (Year: 2021).*

Keren-Shaul (Keren-Shaul et al. (Jun. 2019) MARS-seq2.0: an experimental and analytical pipeline for indexed sorting combined with single cell sequencing. Nature Protocols vol. 14, p. 1841-1862). (Year: 2019).*

Bonacci, et al., "Modularity of a Carbon-Fixing Protein Organelle", In Proceedings of the National Academy of Sciences, vol. 109, Issue 2, Jan. 10, 2012, pp. 478-483.

Cao, et al., "De Novo Design of Picomolar SARS-CoV-2 Miniprotein Inhibitors", In Journal of Science, vol. 370, Issue 6515, Oct. 23, 2020, 7 Pages.

Jumper, et al., "Highly Accurate Protein Structure Prediction with AlphaFold", In Journal of Nature, vol. 596, Issue 7873, Aug. 26, 2021, pp. 583-589.

Peterman, et al., "Sort-Seq under the Hood: Implications of Design Choices on Large-Scale Characterization of Sequence-Function Relations", In Journal of BMC Genomics, vol. 17, Mar. 9, 2016, pp. 1-17.

Reich, et al., "SORTCERY—A High-Throughput Method to Affinity Rank Peptide Ligands", In Journal of Molecular Biology, vol. 427, Issue 11, Jun. 5, 2015, pp. 2135-2150.

Yang, et al., "Machine-Learning-Guided directed Evolution for Protein Engineering", In Journal of Nature Methods, vol. 16, Issue 8, Aug. 2019, pp. 687-694.

Zhang, et al., "Genome Design of Hybrid Potato", In Journal of Cell, vol. 184, Issue 15, Jul. 22, 2021, pp. 3873-3883.

"International Search Report and Written Opinion Issued in PCT Application No. PCT/US2022/048522", Mailed Date: Mar. 3, 2023, 17 Pages.

Trippe, et al., "Randomized Gates Eliminate Bias in Sort-Seq Assays", In Journal of Protein Science, vol. 31, Issue 9, Sep. 30, 2022, 8 Pages.

* cited by examiner

300A

Density

LOG (Fluorescence value)

True Distribution Mean Values

| | |
|---|---|
| Cell Group A 302 | 0.06 |
| Cell Group B 304 | 0.44 |
| Cell Group C 306 | 0.70 |
| Cell Group D 308 | 0.97 |

Probability

Bin A 310   Bin B 312   Bin C 314   Bin D 316

LOG (Fluorescence value)

Cell Count

| | Bin A | Bin B | Bin C | Bin D |
|---|---|---|---|---|
| Cell Group A 302 | 422 | 7 | 0 | 0 |
| Cell Group B 304 | 12 | 150 | 76 | 0 |
| Cell Group C 306 | 0 | 2 | 53 | 121 |
| Cell Group D 308 | 0 | 0 | 0 | 300 |

Probability

Bin A 320   Bin B 322

LOG (Fluorescence value)

Cell Count

| | Bin A 320 | Bin B 322 |
|---|---|---|
| Cell Group A 302 | 429 | 0 |
| Cell Group B 304 | 119 | 119 |
| Cell Group C 306 | 50 | 126 |
| Cell Group D 308 | 0 | 300 |

FIG. 3F

400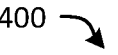

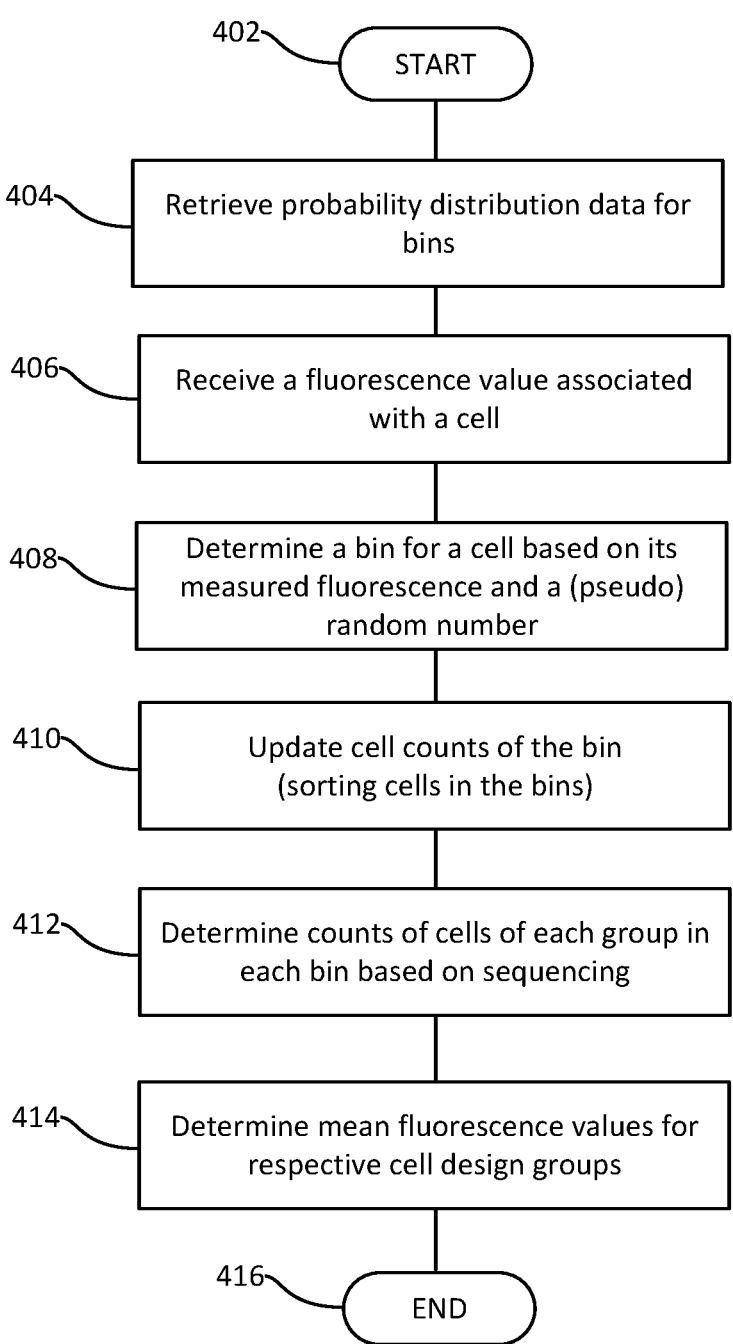

402   START

404   Retrieve probability distribution data for bins

406   Receive a fluorescence value associated with a cell

408   Determine a bin for a cell based on its measured fluorescence and a (pseudo) random number 410   Update cell counts of the bin (sorting cells in the bins)

412   Determine counts of cells of each group in each bin based on sequencing

414   Determine mean fluorescence values for respective cell design groups

416   END

FIG. 4

UNBIASED SORTING AND SEQUENCING OF OBJECTS VIA RANDOMIZED GATING SCHEMES

BACKGROUND

Identifying different types of cell designs with accuracy through cell sorting and sequencing a library of cell designs has become popular for determining physical and chemical characteristics of cells. For example, a "sort-seq assay" method is a popular method for sorting a mixture of cells with various cell designs (e.g., different proteins or protein variants encoded by different DNA sequences) and for separating collections of cells with distinct cell designs across a plurality of tubes. Each cell design exhibits a characteristic intensity or value of fluorescence when bound to a fluorescent marker, so the "sort-seq assay" method uses fluorescence activated cell sorting (FACS) to sort cells into the plurality of tubes. However, there is a level of imprecision or error (i.e., variability) in the fluorescence values such that each tube is likely to include varying cell counts of cells with different cell designs. Since the "sort-seq assay" sorts the cells into a finite set of tubes (e.g., 2-6 tubes), a histogram approach has traditionally been used to determine a distribution of the different cell designs across a plurality of "bins" (e.g., 2-6 bins) corresponding to the plurality of tubes. For instance, the histogram approach may be used to estimate a mean fluorescence of the cell designs represented in each of the plurality of bins. Multiplexed sequencing may then be performed to determine the underlying deoxyribonucleic acid (DNA) sequences corresponding to the cell designs present in each tube. In aspects, multiplexed sequencing enables a plurality of cell designs to be sequenced simultaneously, reducing time and costs. The technique of using histograms combined with multiplexed sequencing of cells provides analyses of the fluorescence of different cell designs.

However, due to the low number of separation tubes (and corresponding histogram bins), an issue arises because the histogram approach introduces systematic bias in determining the distribution of different cell designs in each tube. As noted above, there is a level of imprecision associated with separating the cells into the different tubes. This imprecision may be due to a number of factors, including similar fluorescence values of different cell designs, variations in fluorescence values for cells of the same cell design, or simply errors in fluorescence detection (e.g., sensor error) or in physically sorting the cells between tubes (e.g., machine error). Since FACS sorts many cells with different measured fluorescence values into the same bin, it is impossible to map DNA sequences for cell design types to the fluorescence values measured for these cells. While the histogram approach may sort cell designs across the tubes, the histogram approach may fail to differentiate between cell designs collected into the same tube. Accordingly, there arises a tension between accuracy and efficiency in the "sort-seq" method including sorting and sequencing of cells. Thus, developing a technology that provides for improved ability to meet the needs of both accuracy and efficiency is desirable.

It is with respect to these and other general considerations that the aspects disclosed herein have been made. In addition, although relatively specific problems may be discussed, it should be understood that the examples should not be limited to solving the specific problems identified in the background or elsewhere in this disclosure.

SUMMARY

Aspects of the present disclosure relate to characterizing a library of cell designs using flow cytometry. The present disclosure solves the issue of accurately characterizing the mean fluorescence for each cell design. For instance, cells may be sorted into bins as a function of their measured fluorescence value. Cell types may be determined based on the moments (e.g., means and variances) of their fluorescence value distributions. In particular, the present disclosure determines mean fluorescence values associated with respective cell design groups using gates which allocate cells into bins using not only their measured fluorescence but also a pseudo-random number input generated by a computer in real time for each cell. A distinct randomized sorting rule corresponds to each bin, so that for each bin a cell is collected into that bin with a probability depending on its fluorescence. Multiplexed DNA sequencing can then be used to determine the number of cells of each cell type in each bin. These counts are combined with the known randomized sorting rules to estimate the mean fluorescence value of each cell design. The resulting estimates of the mean fluorescence values are then more accurate than those obtained with the histogram approach.

In aspects, a "cell design" may refer to a molecule (e.g., a protein) having distinct physical and/or chemical properties. Since protein variants may exhibit different physical and/or chemical properties, protein variants may correspond to different cell designs. Based on these distinct physical or chemical properties, different cell designs may exhibit distinct binding characteristics, which can be detected by exposing the molecule to fluorescent markers, for instance.

As noted above, the "sort-seq assay" method uses fluorescence activated cell sorting (FACS) to sort cells having different cell designs (e.g., different binding characteristics to the fluorescent markers) into different tubes. However, there is a level of imprecision or error (i.e., variability) in the sorting such that each tube is likely to include varying densities (or cell counts) of cells with different cell designs. The disclosed technology uses a set of randomized sorting rules for respective gates, which may be pre-calculated based on a number of gates. In aspects, a pseudo-random number generator generates pseudo-random numbers. A tube determiner determines a physical tube (i.e., a bin, a container, and the like) collecting respective cells according to a randomized sorting rule associated with the bin. The tube determiner may apply a stochastic or randomized gate to count cell counts within a bin based on a probability proportional to a measured fluorescence of each cell design. The disclosed technology uses a sorting rule that incorporates randomness into determining a bin for a cell. Each cell is sorted independently into a bin with a probability that depends on the log fluorescence value exhibited by the cell. Based on the randomized sorting rules of cells predetermined for each bin, unbiased mean fluorescence values for respective cell design groups may be determined based on cell counts of the cell design groups across the bins.

In contrast, traditional methods use discrete, non-continuous histograms with discrete ranges of fluorescence values for allocating cells into bins. For instance, systematic bias is introduced by using a center or a mean of the histogram associated with a bin as a mean value for a group of cells, particularly when the bin includes mixed cell design groups. The traditional methods discredit the (log) fluorescence values associated with the bin because the mean value differs from a true distribution mean of fluorescence values for a group of cells with a particular cell design. That is, the traditional methods raise issues of systematic bias in use of the mean fluorescence values by ignoring variability of cell design groups within each tube, which variability may be caused by any of a number of factors described above. The present disclosure removes the systematic bias by applying randomized sorting rules of cells within each bin. Mean fluorescence values associated with respective cell design groups can be determined based on cell counts of the respective cell design groups across the bins. The mean fluorescence values may be used in characterizing a library of cell designs. The disclosed technology may be implemented as a lab device or apparatus.

In aspects, the present disclosure relates to a method for determining a mean fluorescence value for a cell design group. The method comprises retrieving randomized sorting rules for sorting a cell into one of a plurality of containers, wherein each randomized sorting rule corresponds to each container of the plurality of containers, and wherein the randomized sorting rules include one or more probability values corresponding to a fluorescence value; receiving a measured fluorescence value associated with a cell, wherein the measured fluorescence value corresponds to a light emission of the cell; generating a number for the cell, wherein the number includes either a random number or a pseudo-random number; determining one of the plurality of containers into which the cell is sorted based on a combination of the number and the one or more probability values; determining, based on sequencing of cells including the cell in a container of the plurality of containers, cell counts of the cell design groups across the plurality of containers; and determining, based on a model using the cell counts of the cell design groups across the plurality of containers, a value corresponding to the cell design group. The value includes a mean fluorescence value. The light emission corresponds to a fluorescent emission by the cell in fluorescence activated cell sorting (FACS), and wherein the fluorescence value corresponds to an intensity of an emission of light as a laser beam activates a fluorescently-dyed cell. The randomized sorting rules are based at least on either a statistical model or a machine learning model. The model includes one of a statistical model, a machine learning model, or a random forest. The method further comprises determining, based on either a statistical model of moments or a trained machine learning model, the plurality of randomized sorting rules. The method further comprises determining, based on cell counts of cells in the plurality of containers, the value corresponding to the cell design group. The method further comprises sequentially characterizing, based on mean fluorescence values associated with respective cell design groups, a library of cell design groups, wherein each cell design is distinct.

The present disclosure further relates to a system for determining a value representing a cell design group. The system comprises a processor; and a memory storing computer-executable instructions that when executed by the processor cause the system to: retrieve randomized sorting rules for sorting a cell into one of a plurality of containers, wherein each randomized sorting rule corresponds to each container of the plurality of containers, and wherein the randomized sorting rules include one or more probability values corresponding to a fluorescence value; receive a measured fluorescence value associated with a cell, wherein the measured fluorescence value corresponds to a light emission of the cell; generate a number for the cell, wherein the number includes either a random number or a pseudo-random number; determine one of the plurality of containers into which the cell is sorted based on a combination of the number and the one or more probability values; determine, based on sequencing of cells including the cell in a container of the plurality of containers, cell counts of the cell design groups across the plurality of containers; and determine, based on a model using the cell counts of the cell design groups across the plurality of containers, a value representing the cell design group. The value includes a mean fluorescence value associated with cells in the cell design group. The light emission corresponds to a fluorescent emission of the cell in fluorescence activated cell sorting (FACS). The fluorescence value corresponds to an intensity of an emission of light as a laser beam activates a fluorescent-dyed cell. The plurality of randomized sorting rules is based either a statistical model or a machine learning model, for example. The model includes one of a statistical model, a machine learning model, a random forest, and the like. The computer-executable instructions when executed further cause the system to: determine, based on either a statistical model of moments or a trained machine learning model, the plurality of randomized sorting rules. The computer-executable instructions when executed further cause the system to determine, based on cell counts of cells in a range of fluorescence values in the plurality of containers, the value corresponding to the cell design group. The computer-executable instructions when executed further cause the system to sequentially characterize, based on respective cells sorted across the plurality of containers, a library of cell design groups, wherein each cell design group is distinct.

The present disclosure still further relates to a computer-implemented method. The method comprises generating, based on a predetermined number of a plurality of containers, randomized sorting rules for sorting the cell into one of the plurality of containers using measured fluorescence values of cells, wherein the randomized sorting rules include one or more probability values; measuring a fluorescence value associated with a cell, wherein the fluorescence value corresponds to a light emission of the cell; generating a number corresponding to the cell, wherein the number includes a pseudo-random number; determining one of the plurality of containers into which the cell is sorted based on a combination of the number and one or more probability values at the measured fluorescence value for respective containers according to the randomized sorting rules; based on the determined one of the plurality of containers, based on sequencing of cells in respective containers of the plurality of containers, counts of cells of a cell group across the plurality of containers; and determining, based on a model using the cell counts of cells in the cell group across the plurality of containers, a value corresponding to the cell group. The value includes a mean fluorescence value associated with the cell group. The model includes one of a statistical model, a machine learning model, a random forest, and the like. The light emission corresponds to an emission of a fluorescent agent attached to the cell in fluorescence activated cell sorting (FACS), and wherein the fluorescence value corresponds to an intensity of the emission when a laser beam hits a fluorescent-dyed cell. Each container includes a tube collecting cells according to fluorescence activated cell sorting. The method further comprises, based at least on a ratio of cell counts of cells across the plurality of containers, determining the mean fluorescence value for the cell group, wherein the model includes a statistical model of moments. The method further comprising determining, based on a statistical model, the plurality of randomized sorting rules.

This Summary is provided to introduce a selection of concepts in a simplified form, which is further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the following description and, in part, will be apparent from the description, or may be learned by practice of the disclosure.

BRIEF DESCRIPTIONS OF THE DRAWINGS

Non-limiting and non-exhaustive examples are described with reference to the following figures.

FIGS. 3A-3B illustrate examples of true cell count distributions of distinct cell designs across a range of log fluorescence values in accordance with aspects of the present disclosure.

FIGS. 3C-3D illustrate examples of estimating cell count distributions of distinct cell designs using a traditional histogram approach in accordance with aspects of the present disclosure.

FIGS. 3E-3F illustrate examples of sorting rules of cell counts for distinct cell designs using a randomized gate approach in accordance with aspects of the present disclosure.

FIG. 4 illustrates an example of a method of using a randomized gate approach to determine unbiased mean fluorescence values of cell design groups in accordance with aspects of the present disclosure.

DETAILED DESCRIPTION

Figure 1:
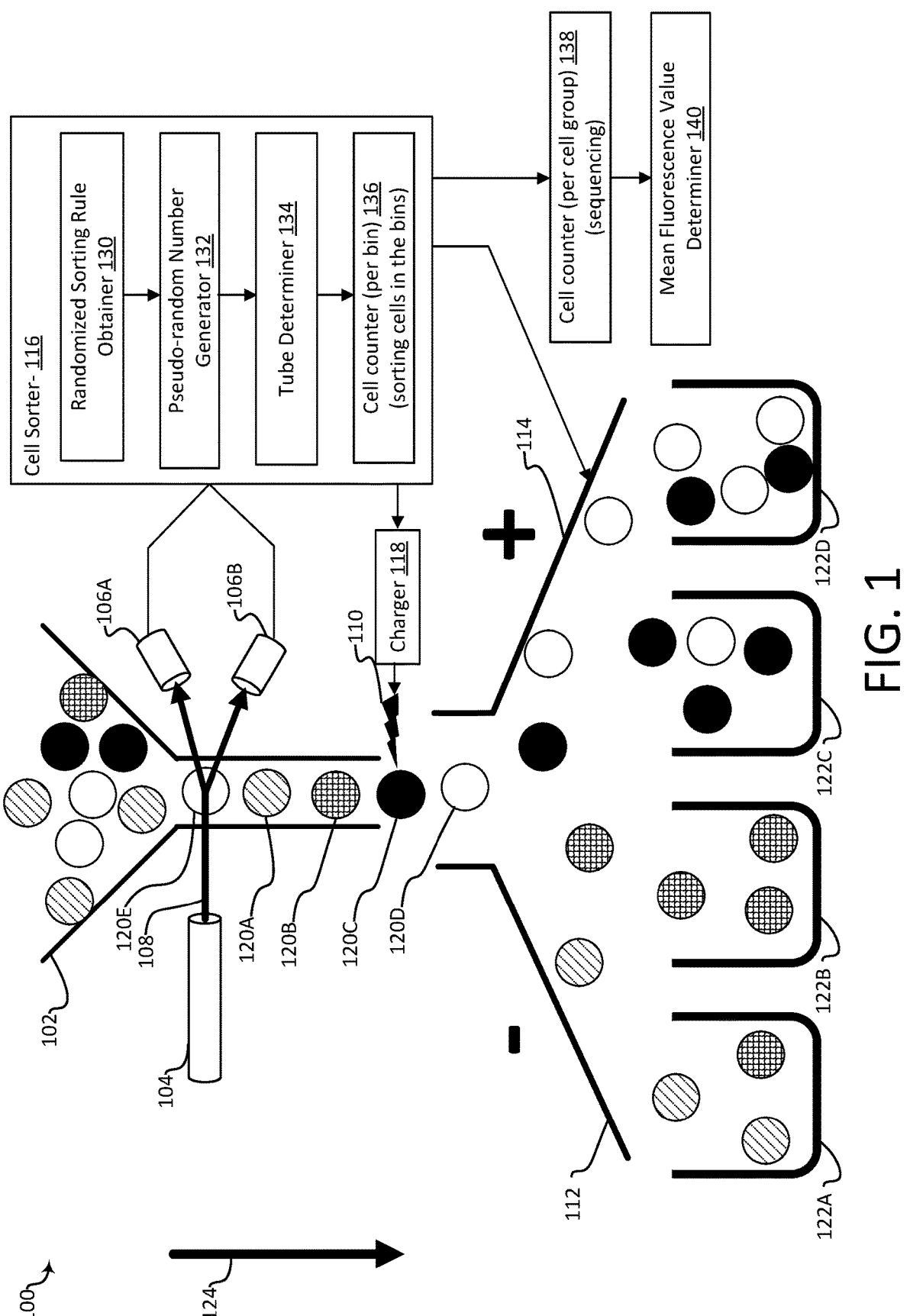
FIG. 1 illustrates an overview of an example system determining cell size and volume in accordance with aspects of the present disclosure.

Various aspects of the disclosure are described more fully below with reference to the accompanying drawings, which form a part hereof, and which show specific example aspects. However, different aspects of the disclosure may be implemented in many different ways and should not be construed as limited to the aspects set forth herein; rather, these aspects are provided so that this disclosure will be thorough and complete, and will fully convey the scope of the aspects to those skilled in the art. Practicing aspects may be as methods, systems, or devices. Accordingly, aspects may take the form of a hardware implementation, an entirely software implementation or an implementation combining software and hardware aspects. The following detailed description is, therefore, not to be taken in a limiting sense.

Sorting cells in a mixture of cells and sequencing a library of cell designs has become a popular task in characterizing cell designs (e.g., protein structures) in biomedical engineering. Measuring and determining cell size and volume has been essential in understanding cell surfaces and intercellular molecules. Flow cytometry includes a method for determining distinct cell designs in a mix of cells with different designs. Fluorescence activated cell sorting (FACS) is a technique in solving protein design problems for which an activity of interest may be linked to a fluorescent signal. A library of cell designs is measured by flow cytometry for sorting cells, and read out using next generation sequencing. These "sort-seq" assays have historically focused on relative enrichments of cell designs. Recently there has been increasing interest in using these assays to provide more quantitative readouts by (1) dividing the space of fluorescence signal into tubes, (2) sorting into these tubes to create a histogram for each design, and then (3) estimating of the mean fluorescence of each design from the histogram. In particular, the histogram defines a bin that collects all cells that indicate particular fluorescence values within a predefined range of fluorescence values. This histogram approach introduces systematic biases and is statistically inefficient because of variability of cells. Variability of fluorescence values as indicated by cells depends not only on distinct cell designs but also on other factors including kinetic variability, noises from sensors, and the like. The traditional systems support discrete gates (i.e., collecting cells with of either probability zero or probability one across a range of fluorescence values) based on respective ranges of fluorescence values without randomness. Rather, the disclosed technology uses gates that represent randomized sorting rules including collection probabilities that vary between zero and one.

The traditional systems use multiplexed sequencing in characterizing a library of cell designs after sorting cells using a histogram. The multiplexed sequencing loses an accuracy of associating a cell design and a tube (or a bin) because of cell-to-cell variability caused by factors other than binding characteristics. Cells with distinct cell types may not necessarily fall into distinct bins of fluorescence values from one another because of the variability and/or bin width. Based on the small number of bins and the large number of different cell groups, the histogram approach used in the traditional systems results in systemic bias when estimating the mean fluorescence of individual cell groups within a bin.

As discussed in more detail below, the present disclosure relates to sorting cells with distinct cell design groups into different physical tubes based on fluorescence values. In particular, the disclosed technology uses a predefined set of randomized sorting rules associated with bins (e.g., containers) based on pseudo-random numbers to specify bins for respective cells in distinct cell design groups. A mean value determiner determines unbiased mean fluorescence values associated with respective cell design groups based on cell counts of the cell design groups in respective bins. Accordingly, the present disclosure enables determining the ratio of cell counts of cells in a cell design group across bins. In this way, a bin (e.g., a container) after sorting may be determined to include cell counts of distinct cell designs at a determined ratio. The disclosed technology estimates mean the fluorescence of distinct types of cell designs based on the cell counts of cells in a cell design group across bins.

In aspects, the disclosed technology determines unbiased estimates of mean fluorescence data by collecting cells according to a randomized value associated with a gate. Sorters sort cells into respective bins according to respective gates based on randomized sorting rules. Sequencers sequence a library of cell designs based on the sorted cells in the bins. Unlike mean values derived from discrete histograms in traditional "sort-seq" methods, these mean estimates have improved accuracy.

FIG. 1 illustrates an overview of an example system 100 for determining bins and mean fluorescence values of cells in accordance with the aspects of the present disclosure. The system 100 includes a cell guide 102, a laser beam emitter 104, light detectors 106A-B, laser beam 108, a charge 110, deflectors (i.e., a negative electromagnet 112 and a positive electromagnet 114), a cell sorter 116, a charger 118, a cell with type A 120A, a cell with type B 120B, a cell with type C 120C, a cell with type D 120D, and tubes 122A-C.

In aspects, the mixture of cells may be dyed with fluorescent markers to distinguish distinct types of cell designs. Cells with distinct types of cell designs may bind the fluorescent markers differently because of distinct molecular structures associated with different cell designs. As a result, cells with distinct cell designs may fluoresce at distinct fluorescence values.

The cell guide guides a flow of a fluid including a mixture of cells 120A-D with distinct cell designs. The fluid flows in toward a direction 124 while the system 100 sorts the mixtures of cells into distinct tubes 122A-D. The mixture of cells in this example includes four distinct types of cell designs: a cell 120A with cell design A, a cell 120B with cell design B, a cell 120C with cell design C, and a cell 120D with cell design D. In aspects, there may be more than four types of cell designs. To sort cells into the four distinct types of cell designs, the system 100 includes four distinct tubes: a tube 122A for collecting cells with cell design A, a tube 122B for collecting cells with cell design B, a tube 122C for collecting cells with cell design C, and a tube 122D for collecting cells with cell design D. In aspects, variability of cells may result in cells of the same cell design having a range of fluorescence values. The system 100 may collect cells of the same cell design type in more than two tubes based on randomized sorting rules associated with respective tubes. For example, the tube 122C includes a mixture of cells with cell designs C and D. The tube 122D includes a mixture of cells with cell design C and D.

The laser beam emitter 104 emits a laser beam 108 at a cell 120E as the cells pass through the cell guide 102. As the laser beam 108 hits and activates the cell 120E, the cell 120E emits fluorescence. In aspects, the fluorescence is the emission of light by the cell 120E absorbing the laser beam 108. The light detectors 106A-B respectively detect the fluorescence. In aspects, the light detectors 106A-B may respectively provide a fluorescence value that corresponds to a cell as each cell passes through the laser beam 108 along the cell guide 102. In some other aspects, the light detectors 106A-B may respectively determine size of cells and fluorescence values associated with the cells.

The cell sorter 116 determines a bin into which each of the cells is directed (or sorted) using data from the light detectors 106A-C. In aspects, the cell sorter 116 includes a randomized sorting rule obtainer 130, a pseudo-random number generator 132, a tube determiner 134, and a cell counter (per bin) 136 in the respective bins, a cell counter (per cell group) 138 (sequencing), and a mean fluorescence determiner 140. In aspects, the cell sorter 116 may drive the charger 118 to charge each cell. The cell sorter 116 may further control deflectors (i.e., the negative electromagnet

112 and the positive electromagnet 114), to guide the charged cells into one of tubes 122A-D.

The randomized sorting rule obtainer 130 obtains randomized sorting rules (e.g., traces) associated with gates (i.e., bins). In aspects, the randomized sorting rules may be predetermined based on a number of gates. For example, the disclosed technology obtains a particular set of randomized sorting rules across fluorescence values for respective bins when there are two bins. In some aspects, there may be a condition where a sum of probability values associated with respective bins at a fluorescence value may be equal to one (i.e., a sum of the probability percentages that a cell is assigned into one of the two bins is equal to 100%). The present disclosure is not limited to determining randomized sorting rules for two gates (or bins, tubes). There may be more than two bins. In aspects, the disclosed technology may store predetermined sets of randomized sorting rules. The randomized sorting rule obtainer 130 may obtain a set of randomized sorting rules based on a number of bins being used to sort cells.

A pseudo-random number generator 132 generates pseudo-random numbers. Use of the pseudo-random numbers enables collecting a cell with a particular cell design according to a randomized sorting rules associated with respective bins.

The tube determiner 134 may use the pseudo-random number and determines which tube a cell is to be counted. For example, a gate with a randomized sorting rule may correspond to a bin for collecting cells having respective cell design groups. Another gate with another randomized sorting rule may correspond to another bin for collecting cells having respective cell design groups, and the like. In determining which tube a cell indicating a fluorescence value needs to be collected, the tube determiner 134 may use the pseudo-random number and probability values associated with the respective bins.

The tube determiner 134 determines a bin for each cell based on a fluorescence value as detected by the light detectors 106A-B and randomized sorting rules associated with the set of gates as determined by the tube determiner 134. The cell sorter 116 may control the charger 118 and the deflectors (i.e., the negative electromagnet 112 and the positive electromagnet 114), to guide the charged cells into one of tubes 122A-D.

In some aspects, there may be cell variations that affect the way that cells with fluorescence dye fluoresces. First, a distinct sequence and/or cell design with varying binding characteristics may cause a fluorescence variance. The disclosed technology aims at distinguishing cells based on the distinct sequence and/or cell design while minimizing errors caused by sensors or other types of measurement noise. A second variation may be variability in kinetics among cells. The difference in kinetics may be driven by physical differences between cell types (e.g., wild-type versus variants). In aspects, cell-to-cell variability results in a "spread" of cell counts across histograms that are separated by predetermined ranges of fluorescence values.

In aspects, the traditional system uses a histogram approach to correlate cell designs with the sequencing results from respective bins. The histogram approach is based on discrete divisions between bins according to mean fluorescence values. As a result, the traditional FACS systems may lose a direct association between the multiplexed sequencing performed for respective bins and the corresponding cells, which may be subject to a combination of the aforementioned variations within each bin.

The cell counter (per bin) 136 count and determine the number of cells of each cell type in the respective bins based on DNA sequencing. In aspects, a cell count as counted by the cell counter (per bin) 136 may include a mixture of cells with distinct cell designs or cell groups.

The cell counter (per cell design group) 138 counts and determines a number of cells in respective cell design groups in the respective bins. In aspects, the cell counter (per cell design group) 138 counts and determines a number of cell of a cell design group in a bin by sequencing cells in the respective bins.

The mean fluorescence determiner 140 determines a mean fluorescence value associated with a cell design group. In aspects, the mean fluorescence value represents a mean value of a density distribution of fluorescence values associated with a cell design group. For example, the mean fluorescence determiner 140 may determine the mean fluorescence value based on a ratio of cell counts of cells in a cell design group across the tubes (and/or bins). In some other example, the mean fluorescence determiner 140 may determine the mean fluorescence value based on a ratio of cell counts of cells within a predetermined range of measured fluorescence values across the tubes (and/or bins).

In aspects, the disclosed technology provides for improved ability to distinguish between variations of cell designs. In the histogram approach, the cell designs could all be sorted into a particular bin and therefore might not previously have been distinguishable. In contrast to the histogram approach, as used by the traditional systems, the disclosed technology uses randomized sorting rules associated with bins and generates randomized gates for respective bins. A ratio of counts of cells of the same cell design group across bins enables determining a mean fluorescence value of the cells of the same design group.

As will be appreciated, the various methods, devices, applications, features, etc., described with respect to FIG. 1 are not intended to limit the system 100 to being performed by the particular applications and features described. Accordingly, additional controller configurations may be used to practice the methods and systems herein and/or features and applications described may be excluded without departing from the methods and systems disclosed herein.

Figures 2A, 2B:
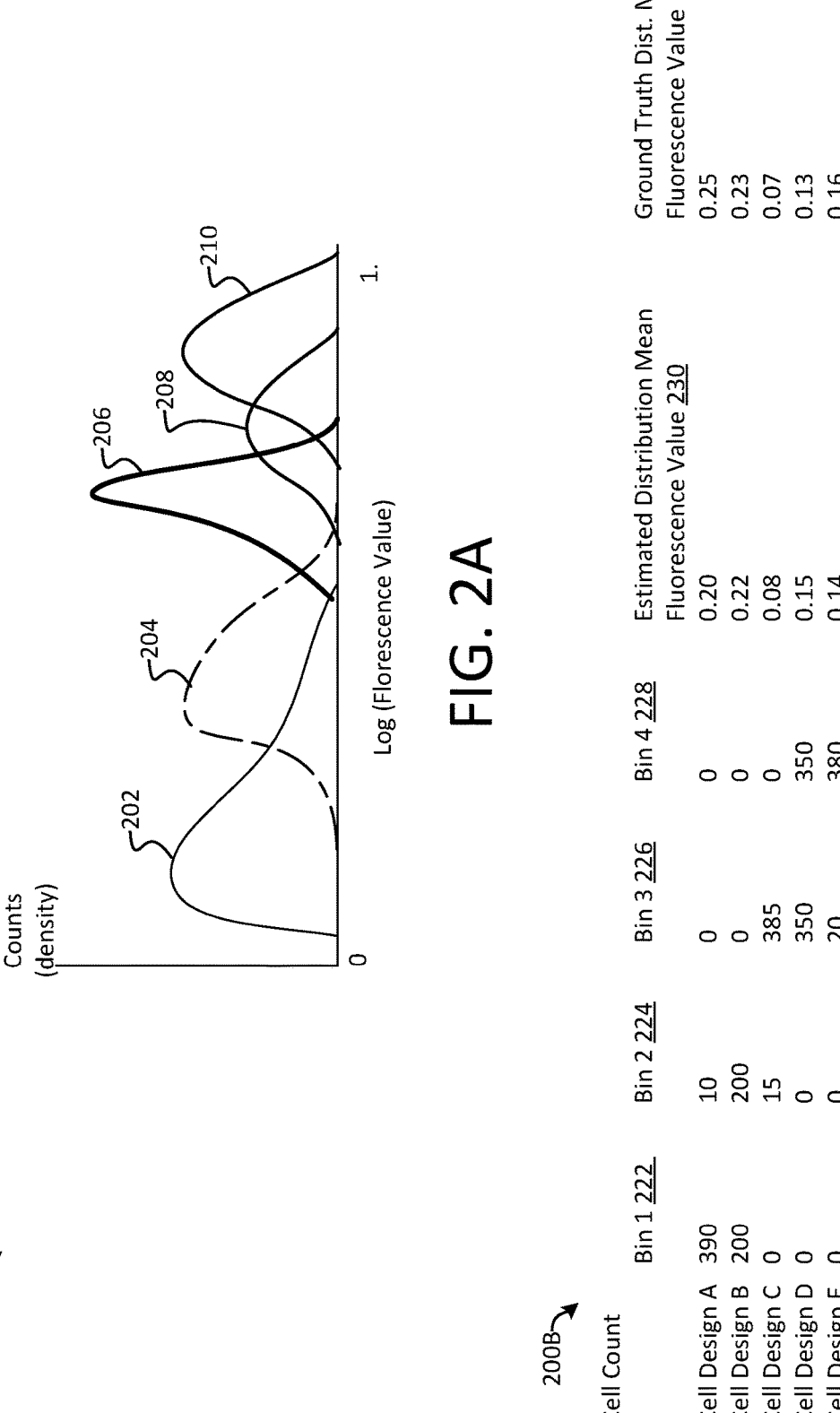
FIG. 2A illustrates an example of true cell count distributions of distinct cell designs across a range of log fluorescence values in accordance with aspects of the present disclosure.
FIG. 2B illustrates an example of mean fluorescence values of respective cell design groups in respective bins in accordance with aspects of the present disclosure.

FIGS. 2A-B illustrate examples of true cell count distributions of distinct cell designs across a range of log fluorescence values (FIG. 2A), and cell counts of different cell designs in different bins with mean fluorescence value calculations for each bin and for individual cell designs (FIG. 2B) in accordance with aspects of the present disclosure. FIG. 2A includes data 200A that indicate true cell count distributions of distinct cell designs across a range of log fluorescence values.

In aspects, a density distribution 202 corresponds to cells with cell design A (e.g., the cell 120A as shown in FIG. 1). A density distribution 204 corresponds to cells with cell design B (e.g., the cell 120B as shown in FIG. 1). A density distribution 206 corresponds to cells with cell design C (e.g., the cell 120C as shown in FIG. 1). A density distribution 208 corresponds to cells with cell design D (not shown in FIG. 1). A density distribution 210 corresponds to cells with cell design E (e.g., the cell 120D as shown in FIG. 1). In aspects, the data 200A indicates distinct density distributions for respective cells with distinct cell designs. Because of the variabilities of respective cells as detailed above, the respective density distributions may overlap. The disclosed technology enables determining bins that corresponds to respective cell design types accurately and efficiently by using gates representing randomized sorting rules (in contrast with use of histograms with discrete divisions at fluorescence values).

In aspects, the present disclosure may characterize at least a part of density distributions based on a number of cells of a cell design group in respective bins. The present disclosure determines mean fluorescence values based on randomized sorting rules associated with respective cell design groups across the respective bins. For example, a mean value determiner may determine a mean fluorescence value associated with a cell design group based on a ratio of cell counts of the cell design group across the bins. In aspects, a mean fluorescence value indicates a mean distribution value of fluorescence values associated with a collection of cells of a same design group.

FIG. 2B illustrates a comparison example of mean fluorescence values calculated for a bin (according to a traditional method) versus true mean fluorescence values of respective cell design groups in the respective bins in accordance with aspects of the present disclosure. Data 200B includes a table of data that indicate counts of each type of cell design in respective bins. In aspects, the bin determiner (e.g., the tube determiner 134 as shown in FIG. 1) determines a bin for each cell based on a set of gates representing randomized sorting rules. The cell counter (per bin) (e.g., the cell counter (per bin) 136 as shown in FIG. 1) counts numbers of cells in the respective bins. The cell counter (per cell group) 138 includes sequencing of the cells in the respective bins. Based on a result of the sequencing of the cells, the cell counter (per cell group) 138 counts number of cells of the respective cell design groups in the respective bins.

The data 200B further indicates estimated mean distribution values 230 that correspond to respective cell designs. In aspects, a mean fluorescence value determiner (e.g., the mean fluorescence value determiner 140) determines mean fluorescence values associated with a cell design group after performing cell sequencing. In some aspects, a mean fluorescence value indicates a mean distribution value of fluorescence values associated with cells of a cell design group.

For example, cell design A has 390 counts in Bin 1 (222), 10 counts in Bin 2 (224), and none in Bin 3 (226) and Bin 4 (228). Cell design B has 200 counts in Bin 1 (222), 200 counts in Bin 2 (224), and none in Bin 3 (226) and Bin 4 (228). Cell design C has no count in Bin 1 (222), 15 counts in Bin 2 (224), 385 counts in Bin 3 (226), and none in Bin 4 (228). Cell design D has no count in Bin 1 (222) and Bin 2 (224), 350 counts in Bin 3 (226), and 350 counts in Bin 4 (228). Cell design E has no count in Bin 1 (222) and Bin 2 (224), 20 counts in Bin 3 (226), and 380 counts in Bin 4 (228). In the example, the mixture of the cells includes 400 counts of cells with each cell design, but the number is not limited. In some other aspects, the mixture of cells may include distinct total numbers of cells with distinct cell designs.

For example, cell design A has its estimated distribution mean fluorescence value 230 of 0.20 and the ground truth mean value (232) of 0.25. The estimated mean value takes into account 390 counts in Bin 1 (222) and 10 counts in Bin 2 (224) respectively. Because of the counts in the respective bins, the estimated distribution mean fluorescence value for the cell design A is 0.20. Similarly, the mean values for the cell design B, C, and D, E are 0.22, 0.08, 0.15, and 0.14 respectively. In contrast, the ground truth distribution mean values (232) corresponding to the respective cell design groups are 0.25, 0.23, 0.07, 0.13, and 0.16. That is, the estimated distribution mean fluorescence values 230 and corresponding values of the ground truth distribution mean fluorescence values 232 are similar.

The traditional systems with the histogram approach for sorting cells do not distinguish mean values for the cell design D and the cell design E because of the non-stochastic soring rules for bin 3 and bin 4. In contrast, the disclosed technology distinguishes the mean values based on cell groups at 0.15 and 0.14 respectively, which are similar to the ground truth distribution mean values of 0.13 and 0.16. Accordingly, the present disclosure with use of randomized sorting rules for gates estimate bins and mean values that more accurately reflect density distributions of respective cells with distinct cell designs than the traditional systems.

As will be appreciated, the various methods, devices, applications, features, etc., described with respect to FIGS. 2A-B are not intended to limit the data 200A and the data 200B to being performed by the particular applications and features described. Accordingly, additional controller configurations may be used to practice the methods and systems herein and/or features and applications described may be excluded without departing from the methods and systems disclosed herein.

FIGS. 3A-3B illustrate examples of true cell count distributions of distinct cell designs across a range of log fluorescence values in accordance with aspects of the present disclosure. FIG. 3A illustrates an example of distributions of densities (i.e., cell counts) of cells with distinct cell designs across a log of fluorescence values. Data 300A indicates a density (i.e., a number of cells) of cells with four distinct groups of cell designs (i.e., Cell Group A, Cell Group B, Cell Group C, and Cell Group D).

FIG. 3B illustrates exemplar true distribution mean values for the four cell groups (i.e., Cell Group A-D) based on the data 300A including density distributions as shown in FIG. 3A. For instance, Cell Group A 302 has a true distribution mean value of 0.06. Cell Group B 304 has a true distribution mean value of 0.44, Cell Group C 306 has a true distribution mean value of 0.70. Cell Group D 308 has a true distribution mean value of 0.97.

FIGS. 3C-3D illustrate examples of estimating cell count distributions of distinct cell designs using a traditional histogram approach in accordance with aspects of the present disclosure. FIG. 3C illustrates an example of use of the histograms for sorting cells into four bins in the traditional systems with the systematic bias. In particular, data 300C indicates four rectangular gates that indicate respective randomized sorting rules having values of either zero or 1, without having overlaps in the randomized sorting rules. The range of log (fluorescence) is divided into four bins without having an overlap: Bin A 310, Bin B 312, Bin C 314, and Bin D 316. Circular shapes represent a number of cells of the four respective groups collected in the respective bins or tubes.

FIG. 3D illustrates an example of true cell counts in bins according to the traditional systems. As shown as data 300D, the Bins A-D correspond to the respective bins in FIG. 3C. For example, Cell Group A 302 corresponds to 329 cells in Bin A, 7 cells in Bin B, and no cell in Bin C and Bin D. Cell Group B 304 corresponds to 12 cells in Bin A, 150 cells in Bin B, 76 cells in Bin C, and no cell in Bin D. Cell Group C 306 corresponds to no cell in Bin A, 2 cells in Bin B, 53 cells in Bin C, and 121 cells in Bin D. The circular shapes as shown in FIG. 3C approximate respective cell counts in data 300D.

FIGS. 3E-3F illustrate examples of randomized sorting rules of cell counts for distinct cell designs using a randomized gate approach in accordance with aspects of the present disclosure. FIG. 3E illustrates gates representing randomized sorting rules to sort cells in respective bins in accordance with aspects of the present disclosure. Data 300E shows a graph against log (fluorescence value). The graph indicates two randomized sorting rules, each corresponding to Bin A 320 and Bin B 322. The circular shapes illustrate cell counts that approximate the data 300F as shown in FIG. 3F.

FIG. 3F illustrates cell count in respective bins based on gates representing randomized sorting rules in accordance with aspects of the present disclosure. Data 300F indicates cell counts of four cell groups (Cell Group A-D) in respective bins (Bin A 320 and Bin B 322). For example, Cell Group A 302 corresponds to 329 cells in Bin A 320 and no cell in Bin B 322. Cell Group B 304 corresponds to 119 cells in both Bin A 320 and Bin B 322. Cell Group C 306 corresponds to 50 cells in Bin A 320 and 126 cells in Bin B 322. Cell Group C 308 corresponds to no cell in Bin A 320 and 300 cells in Bin B 322.

FIG. 4 illustrates an example of a method for sorting cells with distinct cell designs in accordance with aspects of the present disclosure. A general order of the operations for the method 400 is shown in FIG. 4. Generally, the method 400 begins with start operation 402 and ends with end operation 416. The method 400 may include more or fewer steps or may arrange the order of the steps differently than those shown in FIG. 4. The method 400 can be executed as a set of computer-executable instructions executed by a computer system and encoded or stored on a computer readable medium. Further, the method 400 can be performed by gates or circuits associated with a processor, an ASIC, an FPGA, a SOC or other hardware device. Hereinafter, the method 400 shall be explained with reference to the systems, components, devices, modules, software, data structures, data characteristic representations, signaling diagrams, methods, etc., described in conjunction with FIGS. 1, 2A-B, 3A-F, 5, and 6A-B.

Following start operation 402, the method 400 begins with a retrieve operation 404, which retrieves randomized sorting rules associated with respective bins. For example, the retrieve operation 404 may retrieve a predetermined set of two randomized sorting rules associated with respective bins when there are two bins. In aspects, the randomized sorting rules may be generated based on a set of predetermined conditions. For example, the conditions may include a sum of probability values across bins at a given fluorescence value is one. A number of bins is not limited to two. There may be more than two bins for collecting cells. A set of probability data associated with respective bins in a case of more than two bins may be based on a predetermined set of conditions. The conditions may include the above exemplary condition associated with a case of having two bins.

In aspects, the disclosed technology may determine randomized sorting rules associated with respective bins based on statistical models including but not limited to a method of moments and a maximum likelihood estimation. Additionally or alternatively, other methods, including methods relying on machine learning may also be used to determine the sorting rules. In aspects, fluorescence values associated with cells of a known cell design type (and/or a known cell group) may be measured and used as true data. The true data may be used as training data to train a model associated with the machine learning. In some aspect, the trained model may predict a bin based on a probability that depends on the log fluorescence value exhibited by a cell. For example, the model may include a neural network, a transformer model, a random forest, and the like. In aspects, the randomized sorting rules are based at least on either a statistical model or a machine learning model. In some aspects, the machine learning model may determine the randomized sorting rules.

Receive operation 406 receives a measured fluorescence associated with a cell. In aspects, the detectors (e.g., the light detectors 106A-B as shown FIG. 1) measures fluorescence and counts the number of cells as a mixture of cells in a fluid passes through the laser beam along a cell guide. As detailed above, there may be variability that causes variations in ways of fluorescence: cells with distinct cell designs, kinetic variability among cells with common binding characteristics, noises, and the like.

Determine operation 408 determines a bin for a cell based on its measured fluorescence and a (pseudo) random number. The determine operation 408 may generate a random or a pseudo-random number. In aspects, the determine operation 408 uses the random or the pseudo-random number to determine a bin based on the set of randomized sorting rules associated with the respective bins. For example, when probability values associated with the respective two bins both indicate 0.5 for a measured fluorescence value of cells, the determine operation 408 may determine a first bin and a second bin at equal number of cells by using the random (or the pseudo-random) numbers.

Update operation 410 updates cell counts for the determined bin. Accordingly, the cell counts for respective bins take into account the randomized sorting rules of respective gates associated with the respective bins. In aspects, cells of an identical design type may be counted in distinct bins because of the randomized sorting rules of each of the distinct bins.

Determine operation 412 determines counts of cells of each group in each bin. In aspects, the counts of cells of each group may include a sum of cell counts of a cell group across bins. In aspects, the determine operation 412 includes sequencing of cells in respective bins. The sequencing of cells identifies cell design groups for respective cells. In some aspects, a cell group may represent cells of an identical design type. In some other aspects, a cell group may represent cells of a plurality of design types. Additionally or alternatively, characteristics of the distributions of each cell design group other than the mean value may be estimated based on the ratios of cell counts in respective bins. For example, variances and higher order moments for each group may be estimated using the same approaches described for estimating means.

Determine operation 414 determines mean values for respective cell design groups based on numbers of cells of the respective cell designs across bins. In aspects, each bin (thus each gate) covers a predetermined range of fluorescence values with variable a randomized sorting rule. In some aspects, randomized sorting rules of gates may overlap. A mean value associated with cells with a cell design may be off the mean of the range of fluorescence values associated with the gate because of the distribution of the counts across bins. In aspects, a mean values associated with cells with a cell design may indicate a mean fluorescence value of a group of cells with a particular cell design.

In aspects, a mean value associated with a cell design group may be based on a ratio of cell counts in respective bins that cover a range of fluorescence values. For example, when all of the bins include a same number of cells of a cell design group, a mean value associated with the cell design group may be a median value of the range of fluorescence values across the bins. Unlike the traditional systems that provide a mean value of a bin, the present disclosure provides a true mean value associated with a cell design group. Accordingly, the disclosed technology improves accuracy of including cells with a targeted cell design group in characterizing the library. In aspects, the determine operation 414 characterizes a library of cells based on the mean value associated with the cell design group. The method 400 ends with an end operation 416.

As should be appreciated, operations 402-416 are described for purposes of illustrating the present methods and systems and are not intended to limit the disclosure to a particular sequence of steps, e.g., steps may be performed in different order, additional steps may be performed, and disclosed steps may be excluded without departing from the present disclosure.

Figure 5:
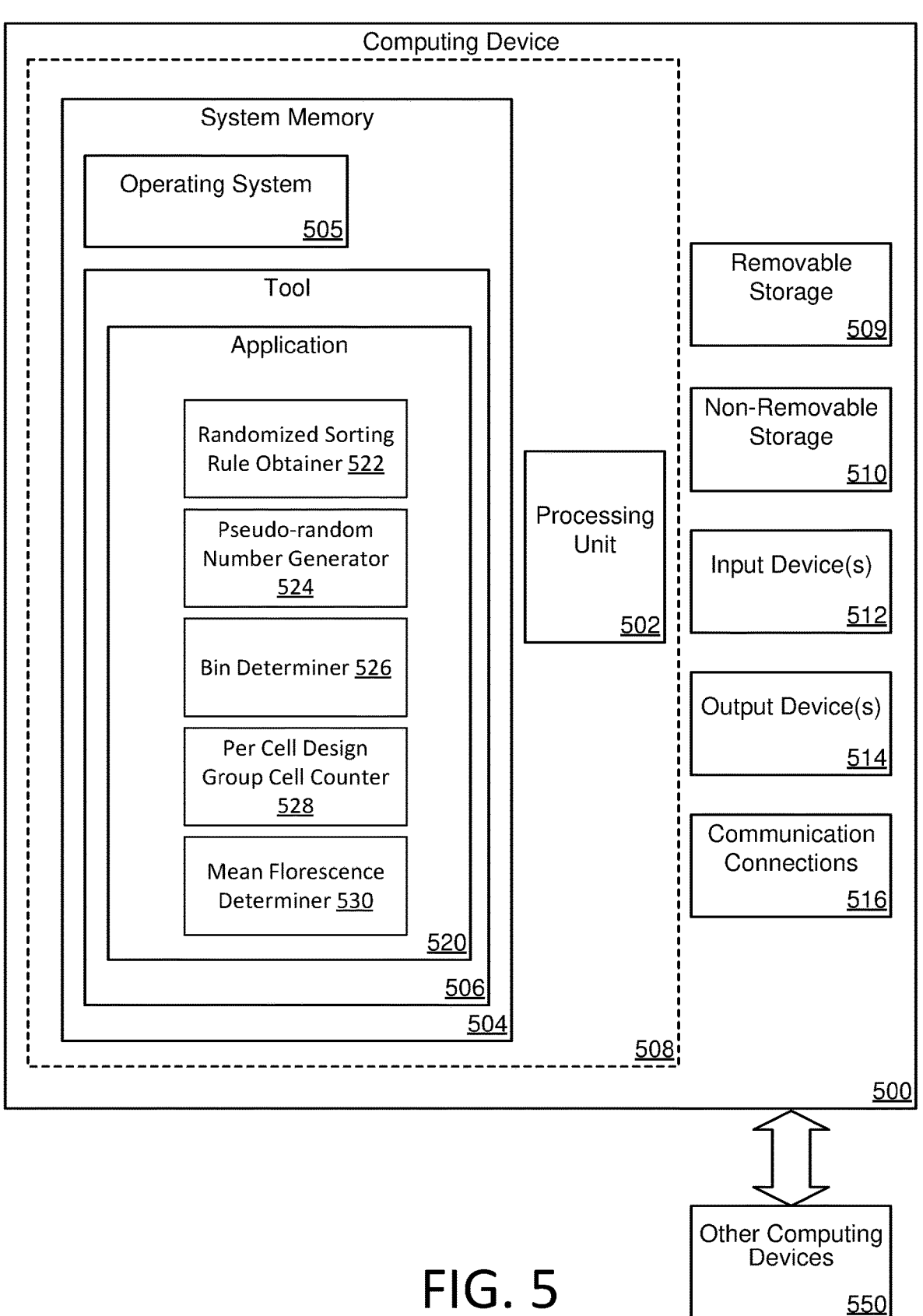
FIG. 5 is a block diagram illustrating example physical components of a computing device with which aspects of the disclosure may be practiced.

FIG. 5 is a block diagram illustrating physical components (e.g., hardware) of a computing device 500 with which aspects of the disclosure may be practiced. The computing device components described below may be suitable for the computing devices described above. In a basic configuration, the computing device 500 may include at least one processing unit 502 and a system memory 504. Depending on the configuration and type of computing device, the system memory 504 may comprise, but is not limited to, volatile storage (e.g., random access memory), non-volatile storage (e.g., read-only memory), flash memory, or any combination of such memories. The system memory 504 may include an operating system 505 and one or more program tools 506 suitable for performing the various aspects disclosed herein such. The operating system 505, for example, may be suitable for controlling the operation of the computing device 500. Furthermore, aspects of the disclosure may be practiced in conjunction with a graphics library, other operating systems, or any other application program and is not limited to any particular application or system. This basic configuration is illustrated in FIG. 5 by those components within a dashed line 508. The computing device 500 may have additional features or functionality. For example, the computing device 500 may also include additional data storage devices (removable and/or non-removable) such as, for example, magnetic disks, optical disks, or tape. Such additional storage is illustrated in FIG. 5 by a removable storage device 509 and a non-removable storage device 510.

As stated above, a number of program tools and data files may be stored in the system memory 504. While executing on the at least one processing unit 502, the program tools 506 (e.g., an application 520) may perform processes including, but not limited to, the aspects, as described herein. The application 520 includes a randomized sorting rule obtainer 522, a pseudo-random number generator 524, a bin determiner 526, a cell counter 528 (per cell design group), and a mean fluorescence determiner 530 as described in more detail with regard to FIG. 1. Other program tools that may be used in accordance with aspects of the present disclosure may include electronic mail and contacts applications, word processing applications, spreadsheet applications, database applications, slide presentation applications, drawing or computer-aided application programs, etc.

Furthermore, aspects of the disclosure may be practiced in an electrical circuit comprising discrete electronic elements, packaged or integrated electronic chips containing logic gates, a circuit utilizing a microprocessor, or on a single chip containing electronic elements or microprocessors. For example, aspects of the disclosure may be practiced via a system-on-a-chip (SOC) where each or many of the components illustrated in FIG. 5 may be integrated onto a single integrated circuit. Such an SOC device may include one or more processing units, graphics units, communications units, system virtualization units, and various application functionality all of which are integrated (or "burned") onto the chip substrate as a single integrated circuit. When operating via an SOC, the functionality, described herein, with respect to the capability of client to switch protocols may be operated via application-specific logic integrated with other components of the computing device 500 on the single integrated circuit (chip). Aspects of the disclosure may also be practiced using other technologies capable of performing logical operations such as, for example, AND, OR, and NOT, including but not limited to mechanical, optical, fluidic, and quantum technologies. In addition, aspects of the disclosure may be practiced within a general-purpose computer or in any other circuits or systems.

The computing device 500 may also have one or more input device(s) 512, such as a keyboard, a mouse, a pen, a sound or voice input device, a touch or swipe input device, etc. The output device(s) 514 such as a display, speakers, a printer, etc. may also be included. The aforementioned devices are examples and others may be used. The computing device 500 may include one or more communication connections 516 allowing communications with other computing devices 550. Examples of the communication connections 516 include, but are not limited to, radio frequency (RF) transmitter, receiver, and/or transceiver circuitry; universal serial bus (USB), parallel, and/or serial ports.

The term computer readable media as used herein may include computer storage media. Computer storage media may include volatile and nonvolatile, removable and non-removable media implemented in any method or technology for storage of information, such as computer readable instructions, data structures, or program tools. The system memory 504, the removable storage device 509, and the non-removable storage device 510 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 500. Any such computer storage media may be part of the computing device 500. Computer storage media does not include a carrier wave or other propagated or modulated data signal.

Communication media may be embodied by computer readable instructions, data structures, program tools, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Figure 6A:
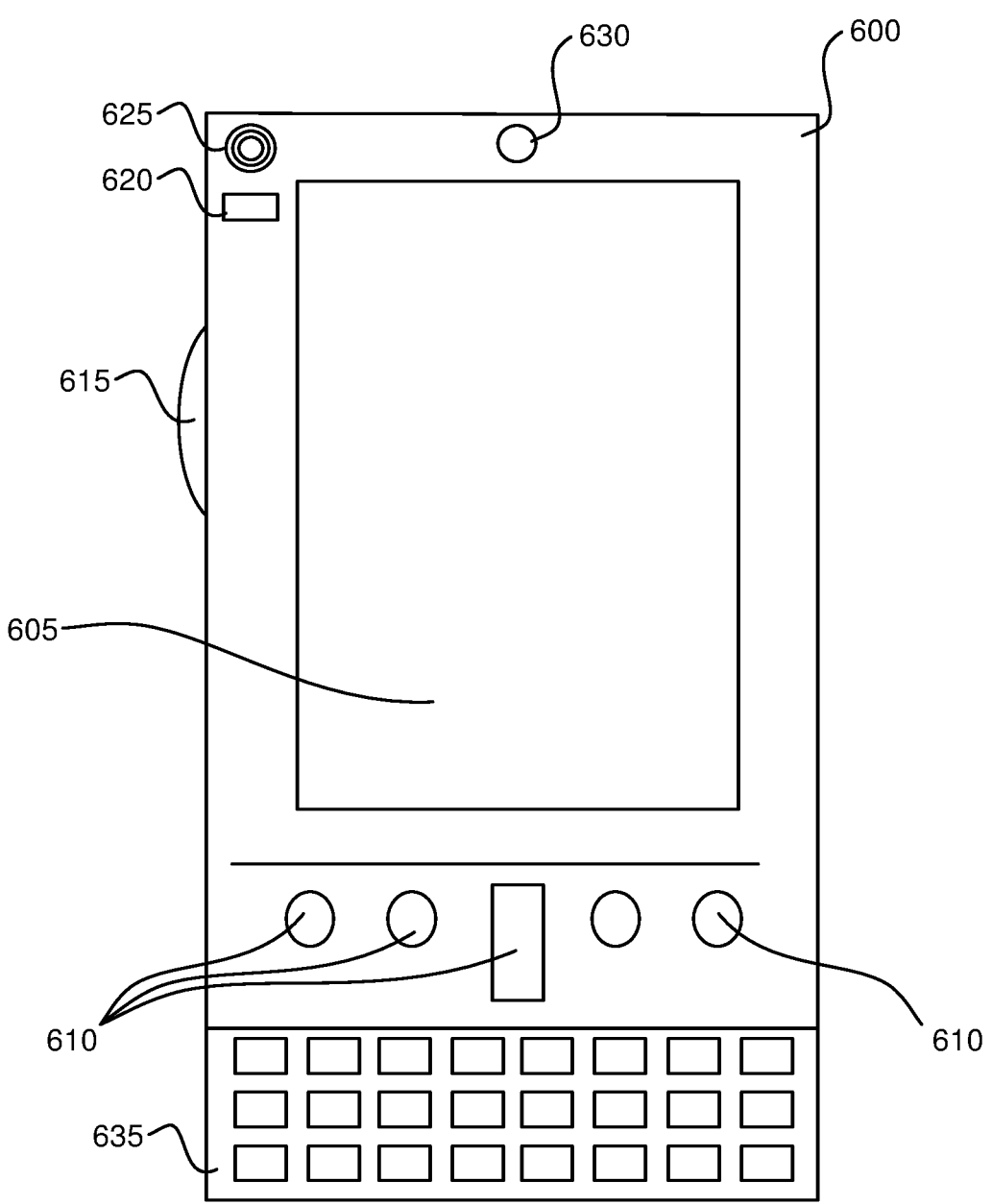
FIG. 6A is a simplified diagram of a mobile computing device with which aspects of the present disclosure may be practiced.
Figure 6B:
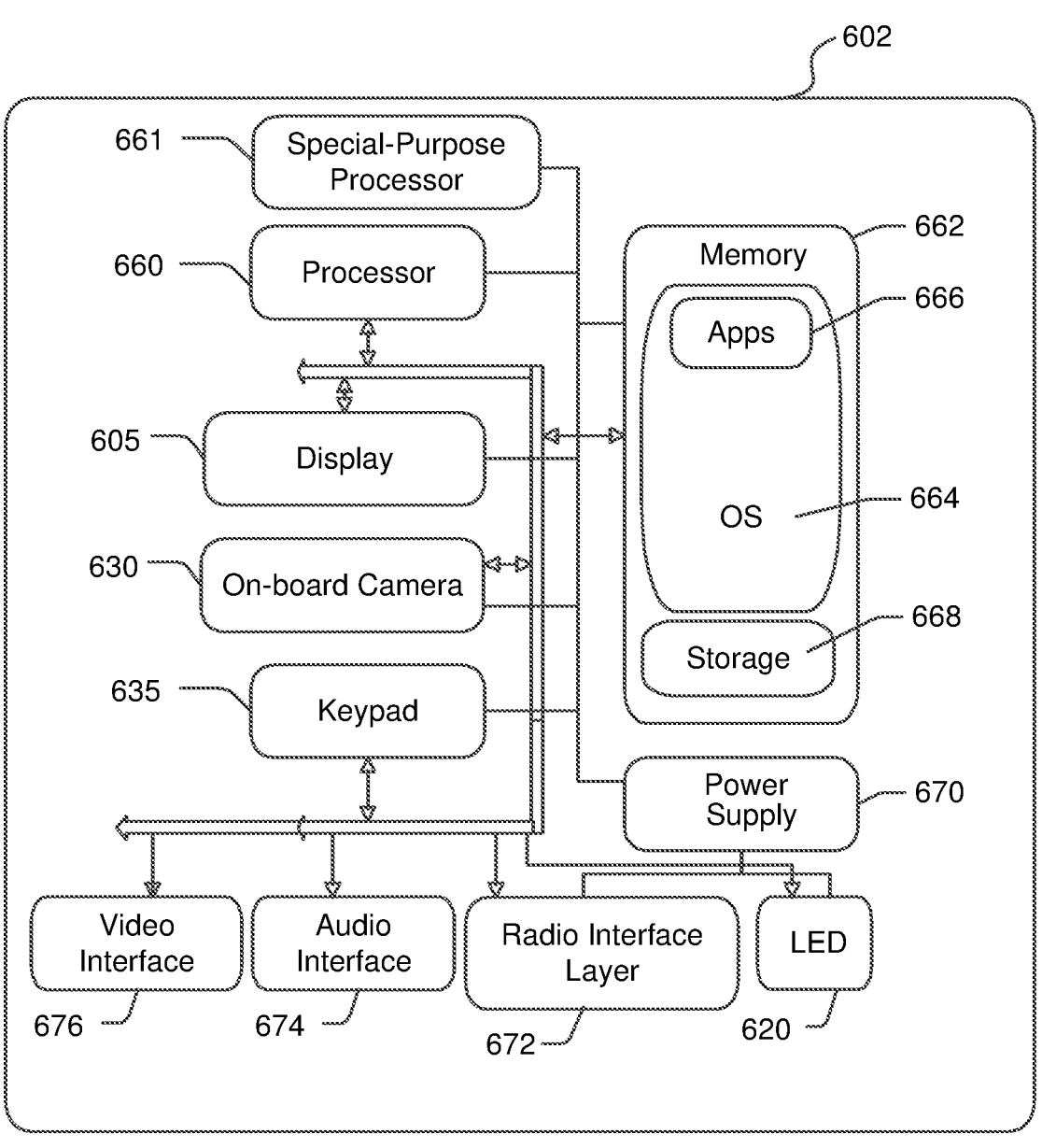
FIG. 6B is another simplified block diagram of a mobile computing device with which aspects of the present disclosure may be practiced.

FIGS. 6A and 6B illustrate a computing device or mobile computing device 600, for example, a mobile telephone, a smart phone, wearable computer (such as a smart watch), a tablet computer, a laptop computer, and the like, with which aspects of the disclosure may be practiced. In some aspects, the client utilized by a user (e.g., an operator of the FACS system as shown as the system 100 in FIG. 1) may be a mobile computing device. With reference to FIG. 6A, one aspect of a mobile computing device 600 for implementing the aspects is illustrated. In a basic configuration, the mobile computing device 600 is a handheld computer having both input elements and output elements. The mobile computing device 600 typically includes a display 605 and one or more input buttons 610 that allow the user to enter information into the mobile computing device 600. The display 605 of the mobile computing device 600 may also function as an input device (e.g., a touch screen display). If included as an optional input element, a side input element 615 allows further user input. The side input element 615 may be a rotary switch, a button, or any other type of manual input element. In alternative aspects, mobile computing device 600 may incorporate more or less input elements. For example, the display 605 may not be a touch screen in some aspects. In yet another alternative aspect, the mobile computing device 600 is a portable phone system, such as a cellular phone. The mobile computing device 600 may also include an optional keypad 635. Optional keypad 635 may be a physical keypad or a "soft" keypad generated on the touch screen display. In various aspects, the output elements include the display 605 for showing a graphical user interface (GUI), a visual indicator 620 (e.g., a light emitting diode), and/or an audio transducer 625 (e.g., a speaker). In some aspects, the mobile computing device 600 incorporates a vibration transducer for providing the user with tactile feedback. In yet another aspect, the mobile computing device 600 incorporates input and/or output ports, such as an audio input (e.g., a microphone jack), an audio output (e.g., a headphone jack), and a video output (e.g., a HDMI port) for sending signals to or receiving signals from an external device.

FIG. 6B is a block diagram illustrating the architecture of one aspect of computing device, a server (e.g., the cell sorter 116 as shown in FIG. 1), a mobile computing device, etc. That is, the mobile computing device 600 can incorporate a system 602 (e.g., a system architecture) to implement some aspects. The system 602 can implemented as a "smart phone" capable of running one or more applications (e.g., browser, e-mail, calendaring, contact managers, messaging clients, games, and media clients/players). In some aspects, the system 602 is integrated as a computing device, such as an integrated digital assistant (PDA) and wireless phone.

One or more application programs 666 may be loaded into the memory 662 and run on or in association with the operating system 664. Examples of the application programs include phone dialer programs, e-mail programs, information management (PIM) programs, word processing programs, spreadsheet programs, Internet browser programs, messaging programs, and so forth. The system 602 also includes a non-volatile storage area 668 within the memory 662. The non-volatile storage area 668 may be used to store persistent information that should not be lost if the system 602 is powered down. The application programs 666 may use and store information in the non-volatile storage area 668, such as e-mail or other messages used by an e-mail application, and the like. A synchronization application (not shown) also resides on the system 602 and is programmed to interact with a corresponding synchronization application resident on a host computer to keep the information stored in the non-volatile storage area 668 synchronized with corresponding information stored at the host computer. As should be appreciated, other applications may be loaded into the memory 662 and run on the mobile computing device 600 described herein.

The system 602 has a power supply 670, which may be implemented as one or more batteries. The power supply 670 might further include an external power source, such as an AC adapter or a powered docking cradle that supplements or recharges the batteries.

The system 602 may also include a radio interface layer 672 that performs the function of transmitting and receiving radio frequency communications. The radio interface layer 672 facilitates wireless connectivity between the system 602 and the "outside world" via a communications carrier or service provider. Transmissions to and from the radio interface layer 672 are conducted under control of the operating system 664. In other words, communications received by the radio interface layer 672 may be disseminated to the application programs 666 via the operating system 664, and vice versa.

The visual indicator 620 (e.g., LED) may be used to provide visual notifications, and/or an audio interface 674 may be used for producing audible notifications via the audio transducer 625. In the illustrated configuration, the visual indicator 620 is a light emitting diode (LED) and the audio transducer 625 is a speaker. These devices may be directly coupled to the power supply 670 so that when activated, they remain on for a duration dictated by the notification mechanism even though the processor 660 and other components might shut down for conserving battery power. The LED may be programmed to remain on indefinitely until the user takes action to indicate the powered-on status of the device. The audio interface 674 is used to provide audible signals to and receive audible signals from the user. For example, in addition to being coupled to the audio transducer 625, the audio interface 674 may also be coupled to a microphone to receive audible input, such as to facilitate a telephone conversation. In accordance with aspects of the present disclosure, the microphone may also serve as an audio sensor to facilitate control of notifications, as will be described below. The system 602 may further include a video interface 676 that enables an operation of an on-board camera 630 to record still images, video stream, and the like.

A mobile computing device 600 implementing the system 602 may have additional features or functionality. For example, the mobile computing device 600 may also include additional data storage devices (removable and/or non-removable) such as, magnetic disks, optical disks, or tape. Such additional storage is illustrated in FIG. 6B by the non-volatile storage area 668.

Data/information generated or captured by the mobile computing device 600 and stored via the system 602 may be stored locally on the mobile computing device 600, as described above, or the data may be stored on any number of storage media that may be accessed by the device via the radio interface layer 672 or via a wired connection between the mobile computing device 600 and a separate computing device associated with the mobile computing device 600, for example, a server computer in a distributed computing network, such as the Internet. As should be appreciated such data/information may be accessed via the mobile computing device 600 via the radio interface layer 672 or via a distributed computing network. Similarly, such data/information may be readily transferred between computing devices for storage and use according to well-known data/information transfer and storage means, including electronic mail and collaborative data/information sharing systems.

The description and illustration of one or more aspects provided in this application are not intended to limit or restrict the scope of the disclosure as claimed in any way. The claimed disclosure should not be construed as being limited to any aspect, for example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

The present disclosure relates to systems and methods for determining a mean fluorescence value for a cell design group according to at least the examples provided in the sections below. The method comprises retrieving randomized sorting rules for sorting a cell into one of a plurality of containers, wherein each randomized sorting rule corresponds to each container of the plurality of containers, and wherein the randomized sorting rules include one or more probability values corresponding to a fluorescence value; receiving a measured fluorescence value associated with a cell, wherein the measured fluorescence value corresponds to a light emission of the cell; generating a number for the cell, wherein the number includes either a random number or a pseudo-random number; determining one of the plurality of containers into which the cell is sorted based on a combination of the number and the one or more probability values; updating a cell count of the determined one of the plurality of containers; determining, based on sequencing of cells including the cell in a container of the plurality of containers, cell counts of the cell design groups across the plurality of containers; and determining, based on a model using the cell counts of the cell design groups across the plurality of containers, a value corresponding to the cell design group. The value includes a mean fluorescence value, wherein the light emission corresponds to a fluorescent emission by the cell in fluorescence activated cell sorting (FACS), and wherein the fluorescence value corresponds to an intensity of an emission of light as a laser beam hits and activates a fluorescent-dyed cell. The randomized sorting rules depend on a predetermined number of containers. The randomized sorting rules are based at least on either a statistical model or a machine learning model. The model includes one of a statistical model, a machine learning model, or a random forest. The method further comprises determining, based on either a statistical model of moments or a trained machine learning model, the plurality of randomized sorting rules. The method further comprises determining, based on cell counts of cells of each cell type in the plurality of containers, the value corresponding to the cell design group. The method further comprises characterizing, based on mean fluorescence values associated with respective cell design groups, a library of cell design groups, wherein each cell design is distinct.

Another aspects of the technology relate to a system for determining a value representing a cell design group. The system comprises a processor; and a memory storing computer-executable instructions that when executed by the processor cause the system to: retrieve randomized sorting rules for sorting a cell into one of a plurality of containers, wherein each randomized sorting rule corresponds to each container of the plurality of containers, and wherein the randomized sorting rules include one or more probability values corresponding to a fluorescence value; receive a measured fluorescence value associated with a cell, wherein the measured fluorescence value corresponds to a light emission of the cell; generate a number for the cell, wherein the number includes either a random number or a pseudo-random number; determine one of the plurality of containers into which the cell is sorted based on a combination of the number and the one or more probability values; determine, based on sequencing of cells including the cell in a container of the plurality of containers, cell counts of the cell design groups across the plurality of containers; and determine, based on a model using the cell counts of the cell design groups across the plurality of containers, a value representing the cell design group. The value includes a mean fluorescence value associated with cells in the cell design group. The light emission corresponds to a fluorescent emission of the cell in fluorescence activated cell sorting (FACS), and wherein the fluorescence value corresponds to an intensity of an emission of light as a laser beam activates a fluorescent-dyed cell. The plurality of randomized sorting rules is based at least on either a statistical model or a machine learning model. The model includes one of a statistical model, a machine learning model, or a random forest. The computer-executable instructions when executed further cause the system to determine, based on either a statistical model or a trained machine learning model, the plurality of randomized sorting rules. The computer-executable instructions when executed further cause the system to sequentially characterize, based on respective cells sorted across the plurality of containers, a library of cell design groups, wherein each cell design group is distinct.

In still further aspects, the technology relates to a computer-implemented method. The method comprises generating, based on a predetermined number of a plurality of containers, randomized sorting rules for sorting the cell into one of the plurality of containers using measured fluorescence values of cells, wherein the randomized sorting rules include one or more probability values; measuring a fluorescence value associated with a cell, wherein the fluorescence value corresponds to a light emission of the cell; generating a number corresponding to the cell, wherein the number includes a pseudo-random number; determining one of the plurality of containers into which the cell is sorted based on a combination of the number and one or more probability values at the measured fluorescence value for respective containers according to the randomized sorting rules; determining, based on sequencing of cells in respective containers of the plurality of containers, counts of cells of a cell group across the plurality of containers; and determining, based on a model using the cell counts of cells in the cell group across the plurality of containers, a value corresponding to the cell group. The value includes a mean fluorescence value associated with the cell group, and wherein the model includes one of a statistical model, a machine learning model, a random forest, and the like. The light emission corresponds to an emission of a fluorescent agent attached to the cell in fluorescence activated cell sorting (FACS), and wherein the fluorescence value corresponds to an intensity of the emission when a laser beam hits a fluorescent-dyed cell. Each container includes a tube collecting cells according to fluorescence activated cell sorting. The method further comprises based at least on a ratio of cell counts of cells at the measured fluorescence value across the plurality of containers, determining the mean fluorescence value for the cell group, wherein the model includes a statistical model of moments. The method further comprises determining, based on a statistical model of moments, the plurality of randomized sorting rules.

Any of the one or more above aspects in combination with any other of the one or more aspect. Any of the one or more aspects as described herein.

What is claimed is:

1. A computer-implemented method for determining a mean fluorescence value for a cell design group, the method comprising:

retrieving a plurality of randomized sorting rules for sorting a cell into one of a plurality of containers as a part of a sort-seq assay of the cell, wherein each randomized sorting rule corresponds to each container of the plurality of containers, and said each randomized sorting rule of the plurality of randomized sorting rules specifies a probability value corresponding to a fluorescence value of said each container;

receiving a measured fluorescence value of the cell, wherein the measured fluorescence value corresponds to a light emission of the cell as captured by a sensor as the part of the sort-seq assay of the cell;

generating a number for the cell, wherein the number includes either a random number or a pseudo-random number according to a randomized sorting rule of the retrieved plurality of randomized sorting rules;

determining a container of the plurality of containers into which the cell is sorted based on a combination of the number and the probability value according to a randomized sorting rule of the container among the plurality of randomized sorting rules, and guiding the cell into the container of the plurality of containers;

determining, based on sequencing of cells including the cell sorted in the container of the plurality of containers, cell counts of respective cell design groups across the plurality of containers, wherein the respective cell design groups describe respective types of cell designs of cells, and a cell design at least describes a protein structure of a cell; and determining, based on a model using the cell counts of the cell design groups across the plurality of containers, a value corresponding to the cell design group, thereby distinguishing the cell of a distinct type of a cell design of the cell design group from other cells with accuracy.

2. The computer-implemented method of claim 1, wherein the value includes the mean fluorescence value, wherein the light emission corresponds to a fluorescent emission by the cell in fluorescence activated cell sorting (FACS), and wherein the fluorescence value corresponds to an intensity of an emission of light as a laser beam activates a fluorescent-dyed cell.

3. The computer-implemented method of claim 1, wherein the plurality of randomized sorting rules are based at least on either a statistical model or a machine learning model.

4. The computer-implemented method of claim 1, wherein the model includes one of a statistical model, a machine learning model, or a random forest.

5. The computer-implemented method of claim 1, the method further comprising:

determining, based on either a statistical model of moments or a trained machine learning model, the plurality of randomized sorting rules.

6. The computer-implemented method of claim 1, the method further comprising:

determining, based on cell counts of cells in a range of fluorescence values in the plurality of containers, the value corresponding to the cell design group.

7. The computer-implemented method of claim 1, the method further comprising:

sequentially characterizing, based on mean fluorescence values associated with respective cell design groups, a library of cell design groups, wherein each cell design is distinct.

8. A system for determining a value representing a cell design group, the system comprising:
   a processor; and
   a memory storing computer-executable instructions that when executed by the processor cause the system to:
      retrieve a plurality of randomized sorting rules for sorting a cell into one of a plurality of containers as a part of a sort-seq assay of the cell, wherein each randomized sorting rule corresponds to each container of the plurality of containers, and said each randomized sorting rule of the plurality of randomized sorting rules specifies a probability value corresponding to a fluorescence value of said each container;
      receive a measured fluorescence value of the cell, wherein the measured fluorescence value corresponds to a light emission of the cell as captured by a sensor as the part of the sort-seq assay of the cell;
      generate a number for the cell, wherein the number includes either a random number or a pseudo-random number according to a randomized sorting rule of the retrieved plurality of randomized sorting rules;
      determine a container of the plurality of containers into which the cell is sorted based on a combination of the number and the probability value according to a randomized sorting rule of the container among the plurality of randomized sorting rules, and guiding the cell into the container of the plurality of containers;
      determine, based on sequencing of cells including the cell sorted in the container of the plurality of containers, cell counts of respective cell design groups across the plurality of containers, wherein the respective cell design groups describe respective types of cell designs of cells, and a cell design at least describes a protein structure of a cell; and
      determine, based on a model using cell counts of the cell design groups across the plurality of containers, the value representing the cell design group, thereby distinguishing the cell of a distinct type of a cell design of the cell design group from other cells with accuracy.

9. The system of claim 8, wherein the value includes a mean fluorescence value associated with cells in the cell design group.

10. The system of claim 8, wherein the value includes a mean fluorescence value, wherein the light emission corresponds to a fluorescent emission of the cell in fluorescence activated cell sorting (FACS), and wherein the fluorescence value corresponds to an intensity of an emission of light as a laser beam activates a fluorescent-dyed cell.

11. The system of claim 8, wherein the plurality of randomized sorting rules is based at least on either a statistical model or a machine learning model.

12. The system of claim 8, wherein the model includes one of a statistical model, a machine learning model, or a random forest.

13. The system of claim 8, the computer-executable instructions when executed further causing the system to:
   determine, based on either a statistical model or a trained machine learning model, the plurality of randomized sorting rules.

14. The system of claim 8, the computer-executable instructions when executed further causing the system to:
   sequentially characterize, based on respective cells sorted across the plurality of containers, a library of cell design groups, wherein each cell design group is distinct.

15. A computer-implemented method, the method comprising:
   generating, based on a predetermined number of a plurality of containers, a plurality of randomized sorting rules for sorting a cell into one of the plurality of containers using measured fluorescence values of cells as a part of a sort-seq assay of the cell, wherein said each randomized sorting rule of the plurality of randomized sorting rules specifies a probability value;
   measuring a fluorescence value of the cell, wherein the fluorescence value corresponds to a light emission of the cell as captured by a sensor as the part of the sort-seq assay of the cell;
   generating a number corresponding to the cell, wherein the number includes a pseudo-random number according to a randomized sorting rule of the plurality of randomized sorting rules;
   determining a container of the plurality of containers into which the cell is sorted based on a combination of the number and the probability value at the measured fluorescence value for respective containers according to the plurality of randomized sorting rules, and guiding the cell into the container of the plurality of containers;
   determining, based on sequencing of cells in respective containers of the plurality of containers, counts of cells of a cell group across the plurality of containers, wherein the cell group describes a type of cell designs of cells, and a cell design at least describes a protein structure of a cell; and
   determining, based on a model using cell counts of cells in the cell group across the plurality of containers, a value corresponding to the cell group, thereby distinguishing the cell of a distinct type of a cell design of the cell group from other cells with accuracy.

16. The computer-implemented method of claim 15, wherein the value includes a mean fluorescence value associated with the cell group, and wherein the model includes one of a statistical model, a machine learning model, or a random forest.

17. The computer-implemented method of claim 15, wherein the light emission corresponds to an emission of a fluorescent agent attached to the cell in fluorescence activated cell sorting (FACS), and wherein the fluorescence value corresponds to an intensity of the emission when a laser beam hits a fluorescent-dyed cell.

18. The computer-implemented method of claim 15, wherein each container includes a tube collecting cells according to fluorescence activated cell sorting.

19. The computer-implemented method of claim 15, the method further comprising:
   based at least on a ratio of cell counts of cells at the measured fluorescence value across the plurality of containers, determining a mean fluorescence value for the cell group, wherein the model includes a statistical model of moments.

20. The computer-implemented method of claim 15, the method further comprising:

determining, based on a statistical model of moments, the plurality of randomized sorting rules.

\* \* \* \* \*